US012617807B2

(12) United States Patent
Merino et al.

(10) Patent No.: US 12,617,807 B2
(45) Date of Patent: May 5, 2026

(54) LONG LASTING OPIOID REVERSAL USING HYDROGEN PEROXIDE-INDUCED RELEASE IN BLOOD

(71) Applicant: University of Cincinnati, Cincinnati, OH (US)

(72) Inventors: Edward Merino, Cincinnati, OH (US); Steve Davidson, Cincinnati, OH (US); Priyangika Senevirathne, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 400 days.

(21) Appl. No.: 18/285,285

(22) PCT Filed: Apr. 1, 2022

(86) PCT No.: PCT/US2022/023095

§ 371 (c)(1),
(2) Date: Oct. 2, 2023

(87) PCT Pub. No.: WO2022/212868

PCT Pub. Date: Oct. 6, 2022

(65) Prior Publication Data

US 2024/0239815 A1 Jul. 18, 2024

Related U.S. Application Data

(60) Provisional application No. 63/169,416, filed on Apr. 1, 2021.

(51) Int. Cl.

| | |
|---|---|
| ***C07F 5/02*** | (2006.01) |
| ***A61K 31/69*** | (2006.01) |
| ***A61P 25/36*** | (2006.01) |

(52) U.S. Cl.

CPC .............. *C07F 5/025* (2013.01); *A61K 31/69* (2013.01); *A61P 25/36* (2018.01)

(58) Field of Classification Search

CPC ....... C07F 5/025; A61K 31/69; A61K 31/485; A61P 25/36; A61P 25/30

See application file for complete search history.

(56) References Cited

U.S. PATENT DOCUMENTS

| | | | | |
|---|---|---|---|---|
| 2008/0234306 | A1 | 9/2008 | Perez et al. | |
| 2013/0289060 | A1 * | 10/2013 | Pasternak | C07D 489/08 514/282 |
| 2019/0231993 | A1 | 8/2019 | Van Sickle et al. | |

OTHER PUBLICATIONS

Klux, Cg et al.) Biocompatible polymeric nanoparticles degrade and release cargo in response to biologically relevant levels of hydrogen peroxide. Journal of American Chemical Society, vol. 134, No. 38, Sep. 26, 2012, doi: 10.1021?a303372u, p. 15758-15764; abstract; p. 3, third paragraph; p. 4, first paragraph; p. 10, scheme 1.

International Search Report mailed Aug. 30, 2022 and Written Opinion in Intl. Patent Application No. PCT/ US2022/023095 filed Apr. 1, 2022. 11 pgs.

* cited by examiner

*Primary Examiner* — Rebecca L Anderson
*Assistant Examiner* — David M Shim
(74) *Attorney, Agent, or Firm* — Brent M. Peebles

(57) ABSTRACT

Naloxone variants that are both long lasting and responsive are disclosed. One version of the compound has a boron ester functional group and the antagonist compound is capable of a sustained release of antagonist based on reaction with hydrogen peroxide. In addition, a method of treating opioid overdose is disclosed. The method involves administering a therapeutically effective amount of the formulation described above to a patient in need thereof. Administration occurs either intranasally, sublingually or intranasally and sublingually, wherein if administration occurs intranasally and sublingually administration occurs simultaneously, sequentially or concomitantly.

4 Claims, 12 Drawing Sheets

FIG. 9B

| | |
|---|---|
| Ref | 0.434882 |
| 200ug/mL standard | 2.119795 |
| 100ug/mL standard | 1.822364 |
| 50ug/mL standard | 1.31927 |
| 25ug/mL standard | 1.003692 |
| 12.5ug/mL standard | 0.840789 |
| 6.25ug/mL standard | 0.617679 |
| 3.125ug/mL standard | 0.5575 |
| 3mg/kg Morphine | 2.307281 |
| 30mg/kg Morphine | 4.578601 |
| 222mg/kg Morphine | 2.943033 |
| Naloxone (6mg/kg) | 0.426407 |
| Prodrug (12 mg/kg) | 0.422498 |
| Morphine (222mg/kg) + Naloxone | 0.417466 |
| Morphine + Prodrug | 0.404518 |
| Saline | 0.455796 |

LONG LASTING OPIOID REVERSAL USING HYDROGEN PEROXIDE-INDUCED RELEASE IN BLOOD

CROSS REFERENCE TO RELATED APPLICATIONS

This application claims priority to U.S. Provisional Application Ser. No. 63/169,416, filed Apr. 1, 2021, and PCT application PCT/US22/23095, which applications are hereby incorporated by reference in their entirety.

TECHNICAL FIELD

The present invention relates generally to the field of opioid receptor antagonists.

BACKGROUND OF THE INVENTION

Opioid overdose is a significant problem that is rising in the US. For example, the rate of opioid overdose death was 13.3 deaths per 100,000 persons in 2016. Ohio has been particularly impacted with a rate three times the national average and greater than 30% annual increases in opioid overdoses for the last four years. One clear issue has been the lack of treatment options. Biochemically, treatment for opioid overdose reversal are opioid receptor antagonists. The most widely used is naloxone, which is most commonly administered intravenously for rapid action and more recently, through nasal sprays. The structure of naloxone is shown in FIG. 1. Naloxone binds to the various opioid receptors (μ, δ, κ) with affinities of 1-15 nM and blocks opioid-induced activation on the same receptors. Unfortunately, naloxone is metabolically instable. Because of naloxone's instability it can lose effectiveness within ~1 hr and often leads to a second overdose event. Especially problematic is that much of the illicit use of opioids now entails synthetic opioids, like fentanyl, that have stronger affinity and longer residence time once bound. As such, a dose of naloxone is metabolized before the receptor's site is open. This causes the need of multiple doses of naloxone and possible death. Thus, there is a strong need for chemical technologies to combat opioid overdose and addiction.

SUMMARY OF THE INVENTION

The present invention addresses that need with a novel modified opioid receptor antagonist compound. In one embodiment, the compound has a boron ester functional group and the antagonist compound is capable of a sustained release of antagonist based on reaction with hydrogen peroxide. In another embodiment, a method of treating opioid overdose is disclosed. The method involves administering a therapeutically effective amount of the formulation described above to a patient in need thereof. Administration occurs either intranasally, sublingually or intranasally and sublingually, wherein if administration occurs intranasally and sublingually administration occurs simultaneously, sequentially or concomitantly.

In one embodiment, the modified opioid receptor antagonist compound has the following structure:

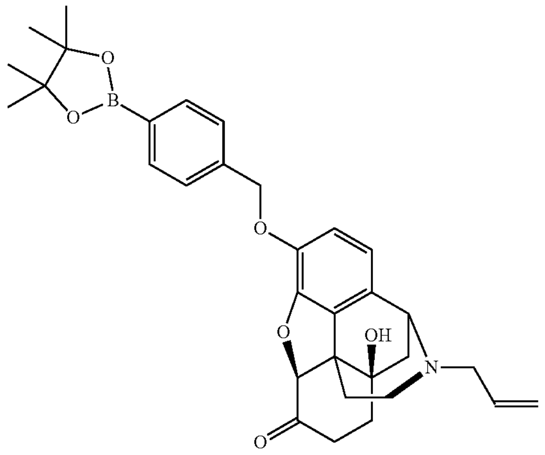

or a pharmaceutically acceptable salt thereof.

In another embodiment of the present invention, the modified opioid receptor antagonist compound has a boronic acid functional group and the compound is capable of a sustained release of antagonist based on reaction with hydrogen peroxide. In another embodiment, a method of treating opioid overdose is disclosed. The method involves administering a therapeutically effective amount of the formulation described above to a patient in need thereof. Administration occurs either intranasally, sublingually or intranasally and sublingually, wherein if administration occurs intranasally and sublingually administration occurs simultaneously, sequentially or concomitantly. In one embodiment, the modified opioid receptor antagonist compound has the following structure:

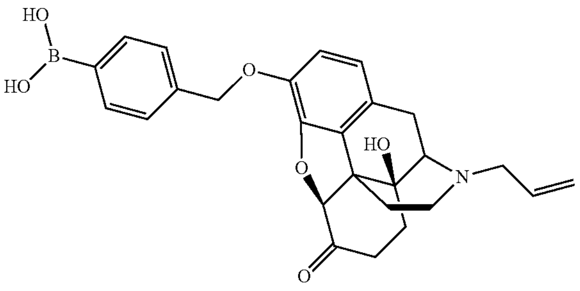

or a pharmaceutically acceptable salt thereof.

BRIEF DESCRIPTION OF THE DRAWINGS

The foregoing summary, as well as the following detailed description of preferred embodiments of the application, will be better understood when read in conjunction with the appended drawings.

FIG. 9B is table of compounds administered to the subjects as described in Example 3.

DETAILED DESCRIPTION OF THE INVENTION

Figure 1:
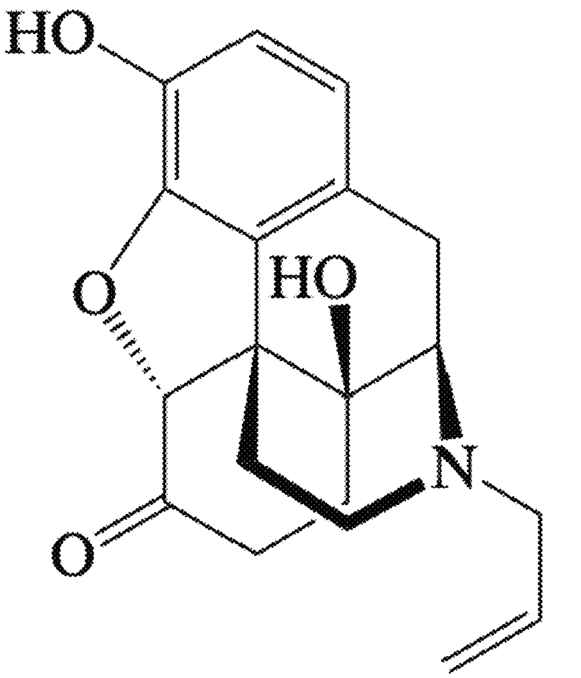
FIG. 1 shows the chemical structure of naloxone.

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms “a,” “an,” and “the” include the plural, and reference to a particular numerical value includes at least that particular value, unless the context clearly dictates otherwise. Ranges may be expressed herein as from “about” or “approximately” one particular value and/or to “about” or “approximately” another particular value. When such a range is expressed, another embodiment includes from the one particular value and/or to the other particular value. Similarly, when values are expressed as approximations, by use of the antecedent “about,” it will be understood that the particular value forms another embodiment.

As used herein, the term “about,” when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term “opioid receptor antagonist” means a substance having a function of preventing an opioid from acting on a receptor.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

In one embodiment, the present invention involves a naloxone variant that is both long lasting and responsive. The invention uses peroxide-induced release that will cause a steady stream of naloxone. This allows the concentration of naloxone to remain high for longer periods of time. In one embodiment of the present invention, hydrogen peroxide sensitive variants of naloxone were designed. In another embodiment, hydrogen peroxide sensitive variants of a stronger antagonist drug, such as Naltrexone, were designed.

Figure 2:
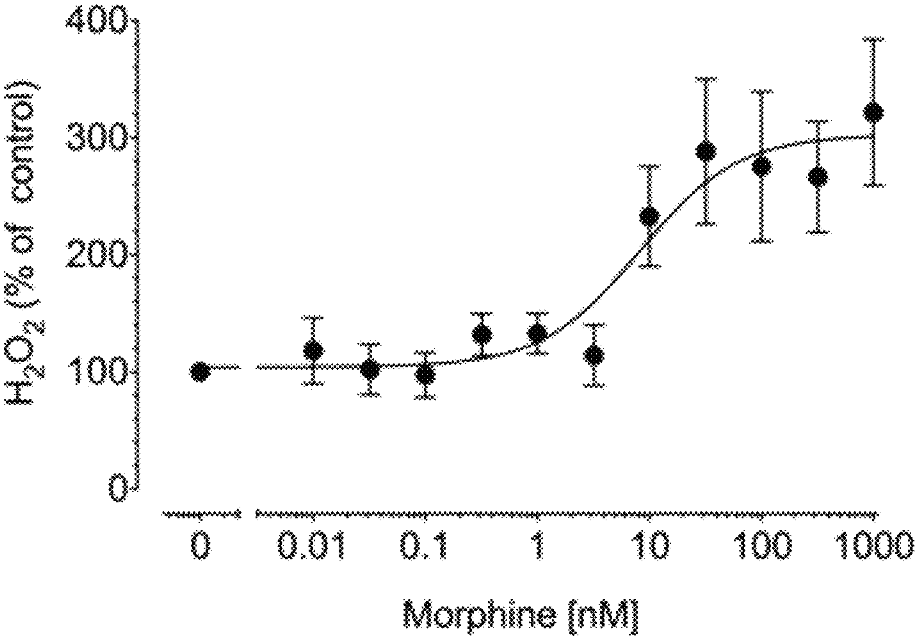
FIG. 2 is a graph showing increasing amounts of opioids induce higher levels of hydrogen peroxide.

The present invention functions by releasing naloxone in the blood by reacting with the hydrogen peroxide present. In a normal person, hydrogen peroxide is present in blood since it is a byproduct of incomplete metabolism. The hydrogen peroxide concentration is estimated to be around 2 μM. In addition, it has been shown that administration of opioids, overdose, and loss of breathing greatly increases the concentrations of hydrogen peroxide. In FIG. 2, a graph shows that the loss of breathing and opioids induce hydrogen peroxide. This increase in peroxide is due to incomplete electron transport metabolism since there is not enough oxygen substrate.

Figure 3:
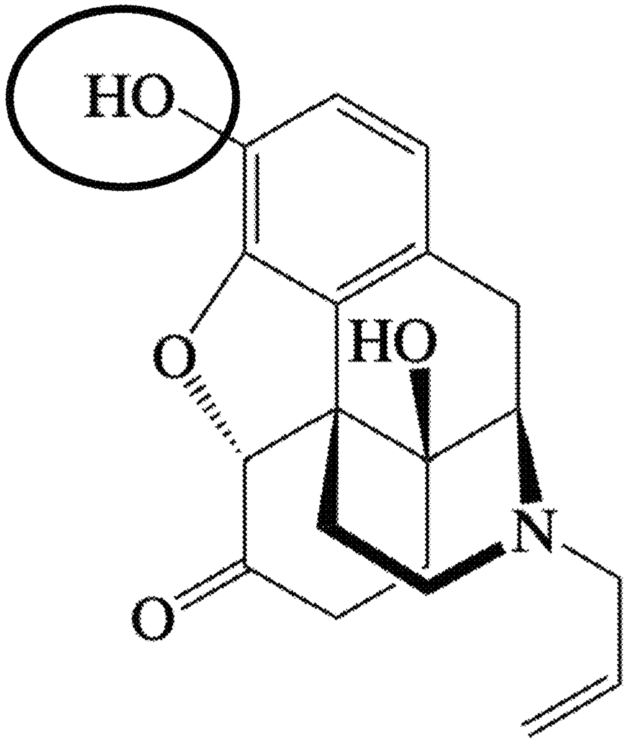
FIG. 3 shows the chemical structure of naloxone, with a red circle indicating the phenol group.

Naloxone fits tightly into the μ-receptor site. Importantly, its modification at the phenol will render naloxone inactive. In FIG. 3, a red circle highlights this phenol portion of naloxone, which is essential for naloxone action and is the most sensitive part of the structure. The present invention synthetically adds groups to the phenol that stabilize it and are sensitive to hydrogen peroxide. The added group reacts with hydrogen peroxide and then releases naloxone over time. This overcomes the short lifetime of naloxone. It can result in sustained concentrations to combat the long residence time of synthetic opioids.

Figure 4:
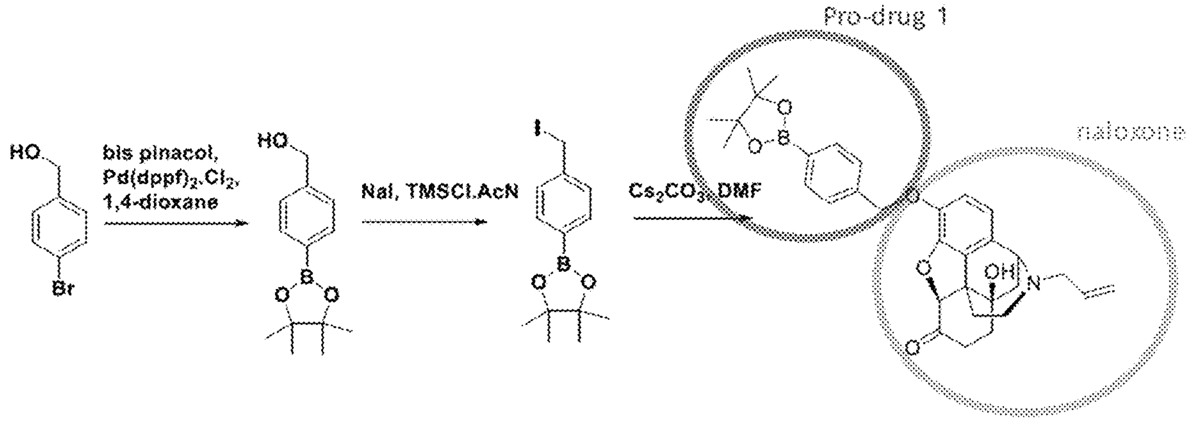
FIG. 4 shows the synthetic pathway for PS-NPD-1.

In one embodiment, the present design is based on boron ester reactivity toward hydrogen peroxide. FIG. 4 shows the synthetic pathway used to create one embodiment of the invention, PS-NPD-1. The structure of PS-NPD-1 is shown in Formula 1.

Formula 1

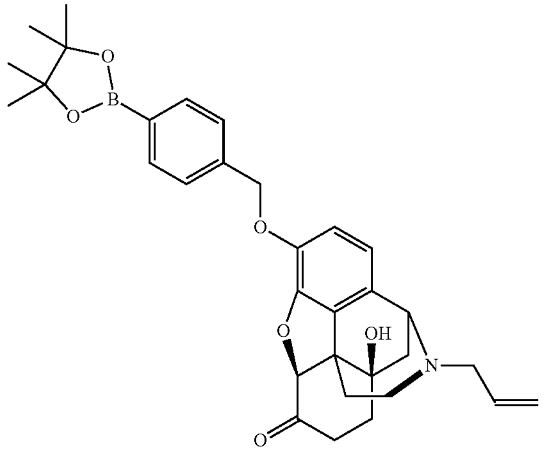

Figure 5:
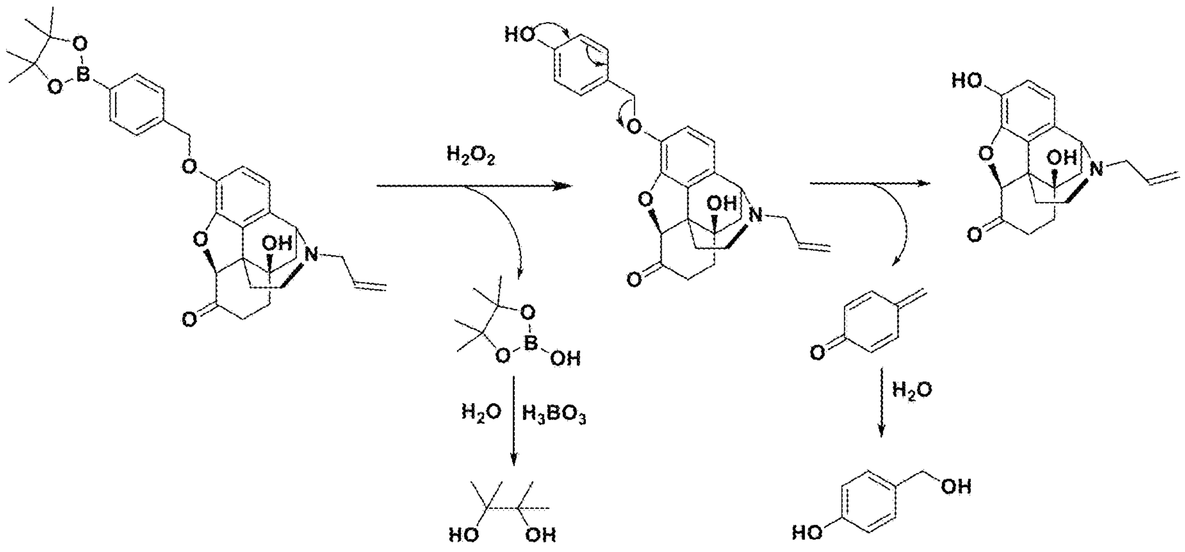
FIG. 5 shows the chemical process whereby PS-NPD-1 releases naloxone in the blood as it is exposed to hydrogen peroxide.

FIG. 5 shows how PS-NPD-1 releases naloxone in the blood as it is exposed to hydrogen peroxide. Its release is tied to the total body metabolism. Cells produce hydrogen peroxide as a by-product of energy production that is transported into the blood. The peroxide leads to the release of naloxone sustained release overtime. As FIG. 2 shows, increasing amounts of opioids induce higher levels of hydrogen peroxide Thus, during overdose even more naloxone will be released.

A second embodiment of the invention, PS-NPD-2 was developed. The structure of PS-NPD-2 is shown in Formula 2.

Formula 2

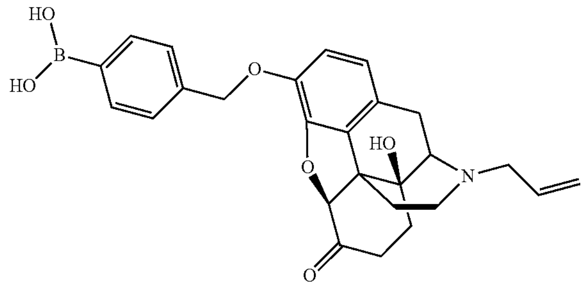

Figure 6:
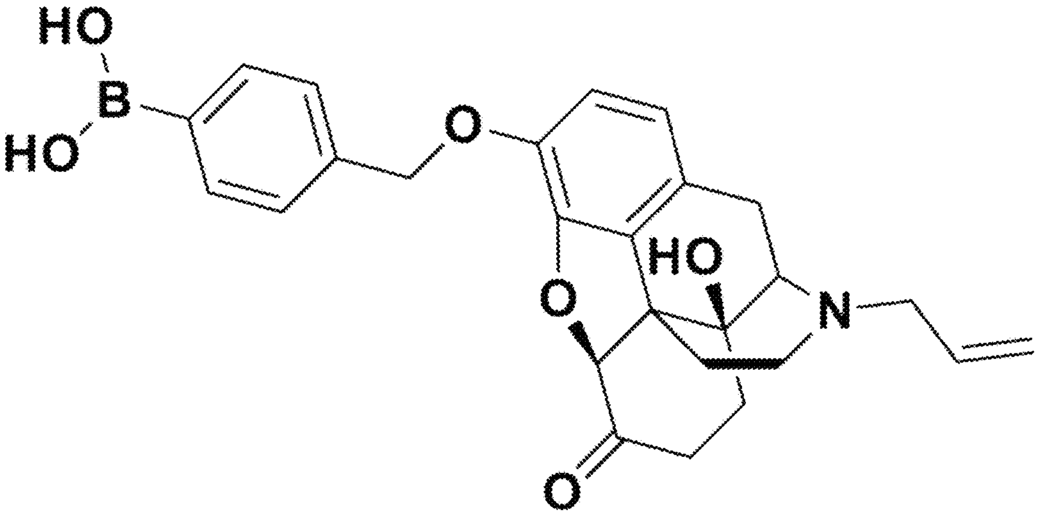
FIG. 6 is the chemical structure of PS-NPD-2.

This structure is also shown in FIG. 6. PS-NPD-2 demonstrates much better solubility than PS-NPD-1. NPD-2 has a max solubility in 1×PBS, 20% PEG400 ~50 mg/mL and thus is able to be formulated easily as an HCl salt.

EXAMPLES

Example 1

Figure 7:
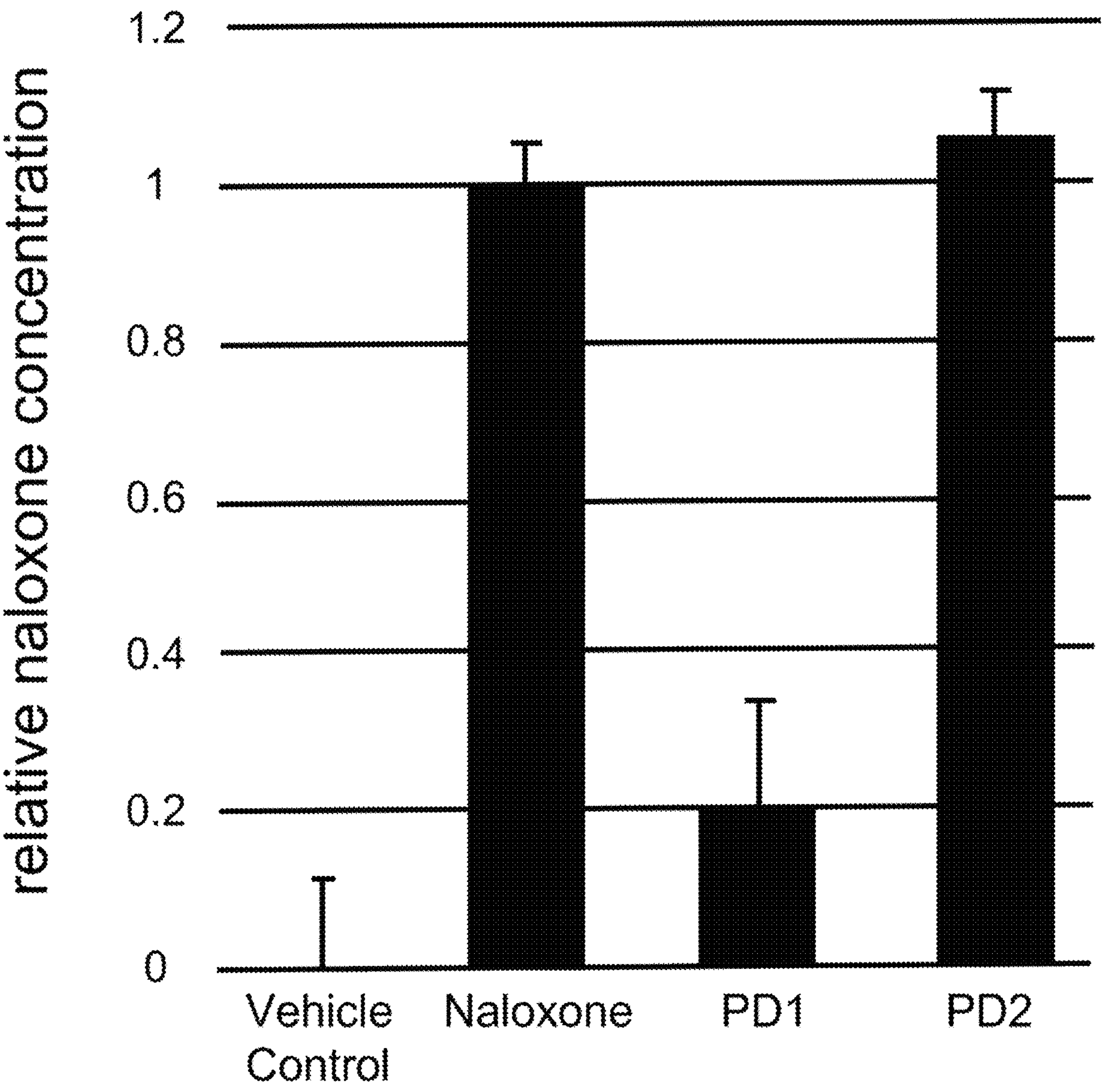
FIG. 7 is a graph showing that PS-NPD-2 produces higher concentrations of naloxone in the blood of mice.

Mice were injected with vehicle, naloxone (6 mg/mL), PS-NPD-1 (10 mg/mL), or PS-NPD-2 salt (12 mg/mL) at time=0. After 30 minutes the mice were sacrificed. Blood was harvested and allowed to coagulate. Serum was harvested. A small amount of naloxone-D5 was spiked in, 9 vol of MeOH were added, and cooled for 30 min. After centrifugation the supernatant from each sample was dried and submitted to LCMS. The results show higher concentrations of naloxone with NPD-2. FIG. 7 is a graph showing the results of the experiment.

Example 2

Figure 8:
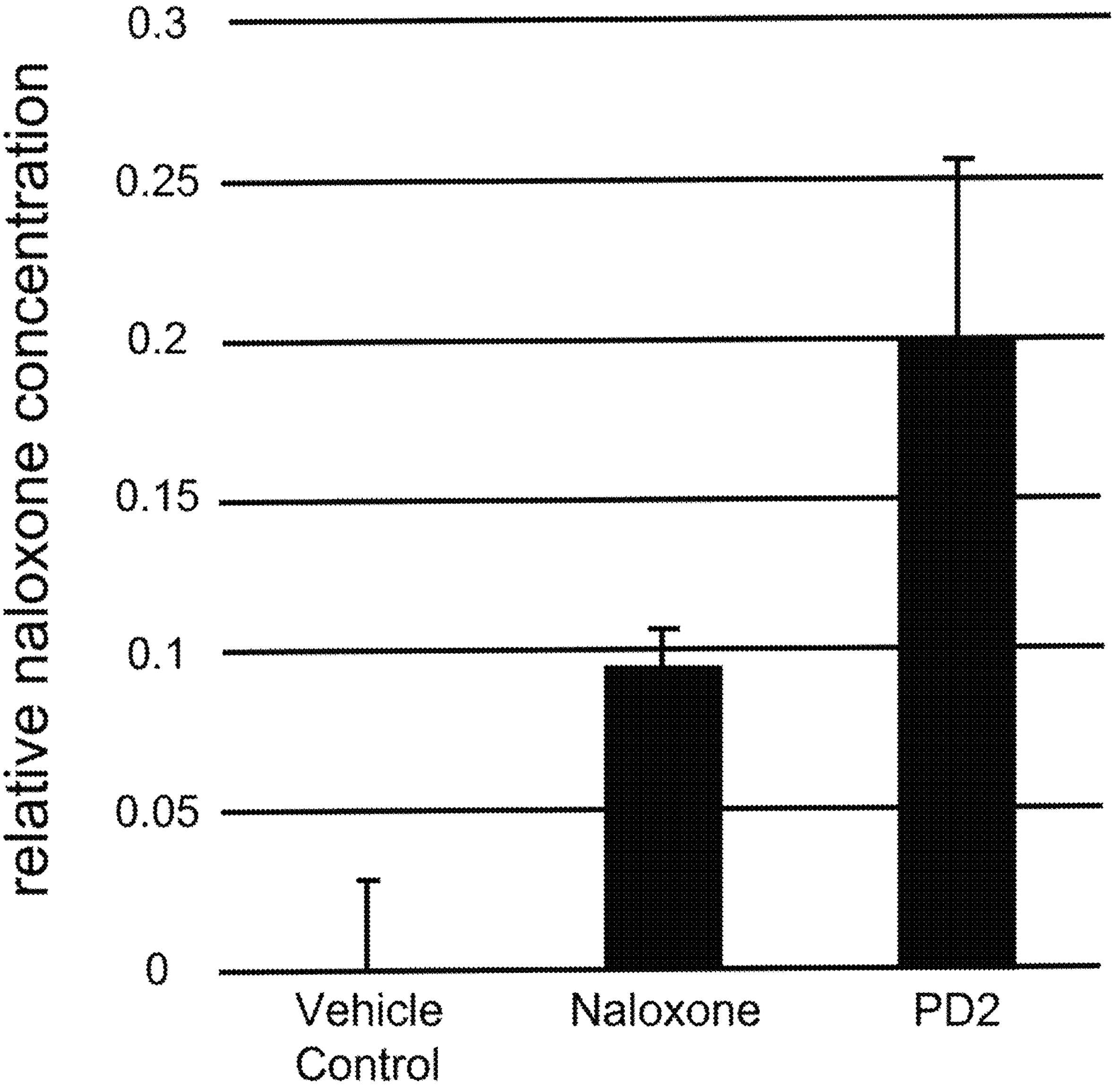
FIG. 8 is a graph showing that, at 2 hours, NPD-2 results in more naloxone in mice blood compared to naloxone.

Another experiment was conducted following the methodology of Example 1, except the mice were sacrificed at 2 hours instead of 30 minutes. FIG. 8 is a graph showing the results of the experiment. The results showed that at 2 hours, NPD-2 resulted in more naloxone in mice blood compared to naloxone. This indicates a potentially longer half-life.

Example 3

Figure 9A:
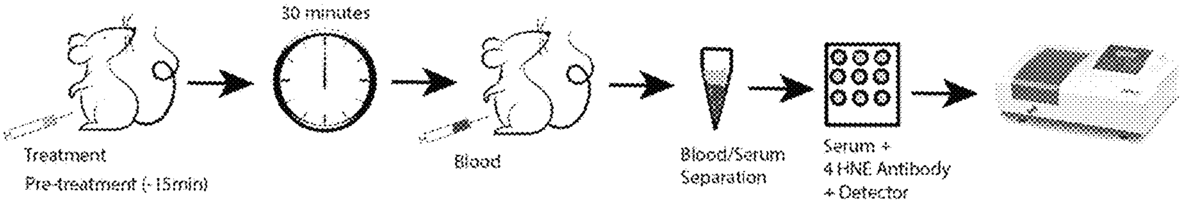
FIG. 9A is an illustration of the experimental process for Example 3.
Figure 9C:
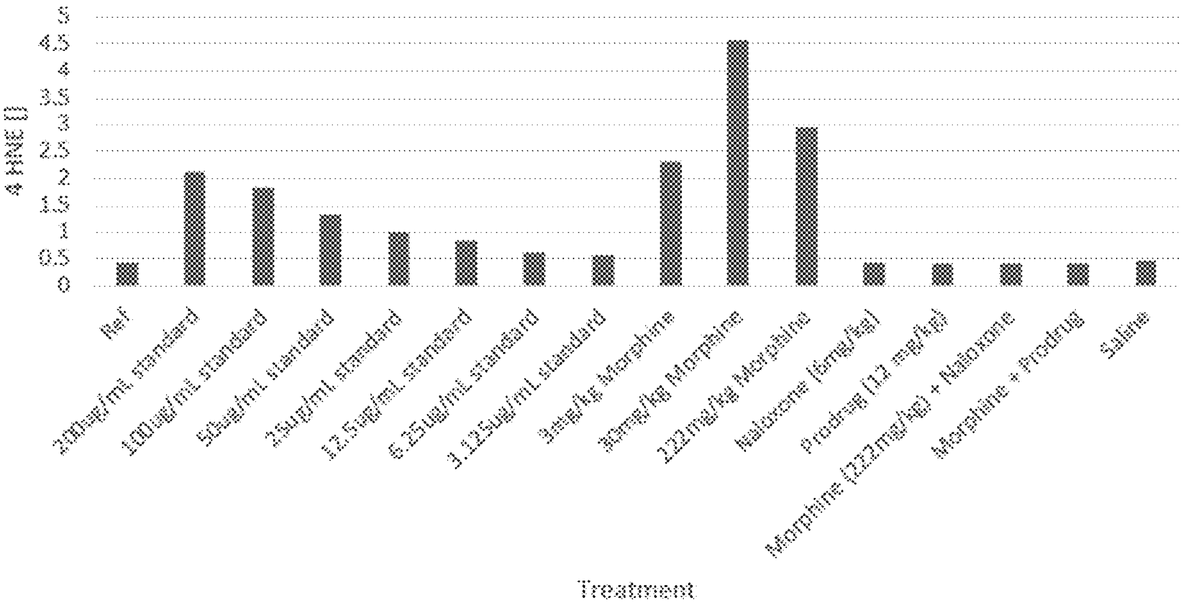
FIG. 9C is a graph showing oxidative stress after opioid/antagonist treatment.

Tests were conducted to examine ROS changes in the blood of mice upon administration of morphine, naloxone, NPD-2, or combinations thereof. This was accomplished using an ELISA assay for 4-NHE that is a marker of ROS damage. See FIG. 9A for an illustration of the process. Mice were administered the given compounds labeled in the plot shown in FIG. 9B. After a short period, serum was collected and quantification of 4-NHE against spiked blood standards was accomplished using an appropriate antibody. The results are shown in FIG. 9C. Administration of morphine increases the ROS more than 10-fold showing that morphine induced high levels of ROS and is thus an appropriate mechanism to activate a prodrug. Addition of naloxone or NPD-2 does not alter the ROS state of mouse blood. Injection of morphine and naloxone or morphine and NPD-2 reduces the ROS levels back to saline treated levels. This data shows that NPD-2 is counteracting opioid induced ROS.

Example 4

Figure 10:
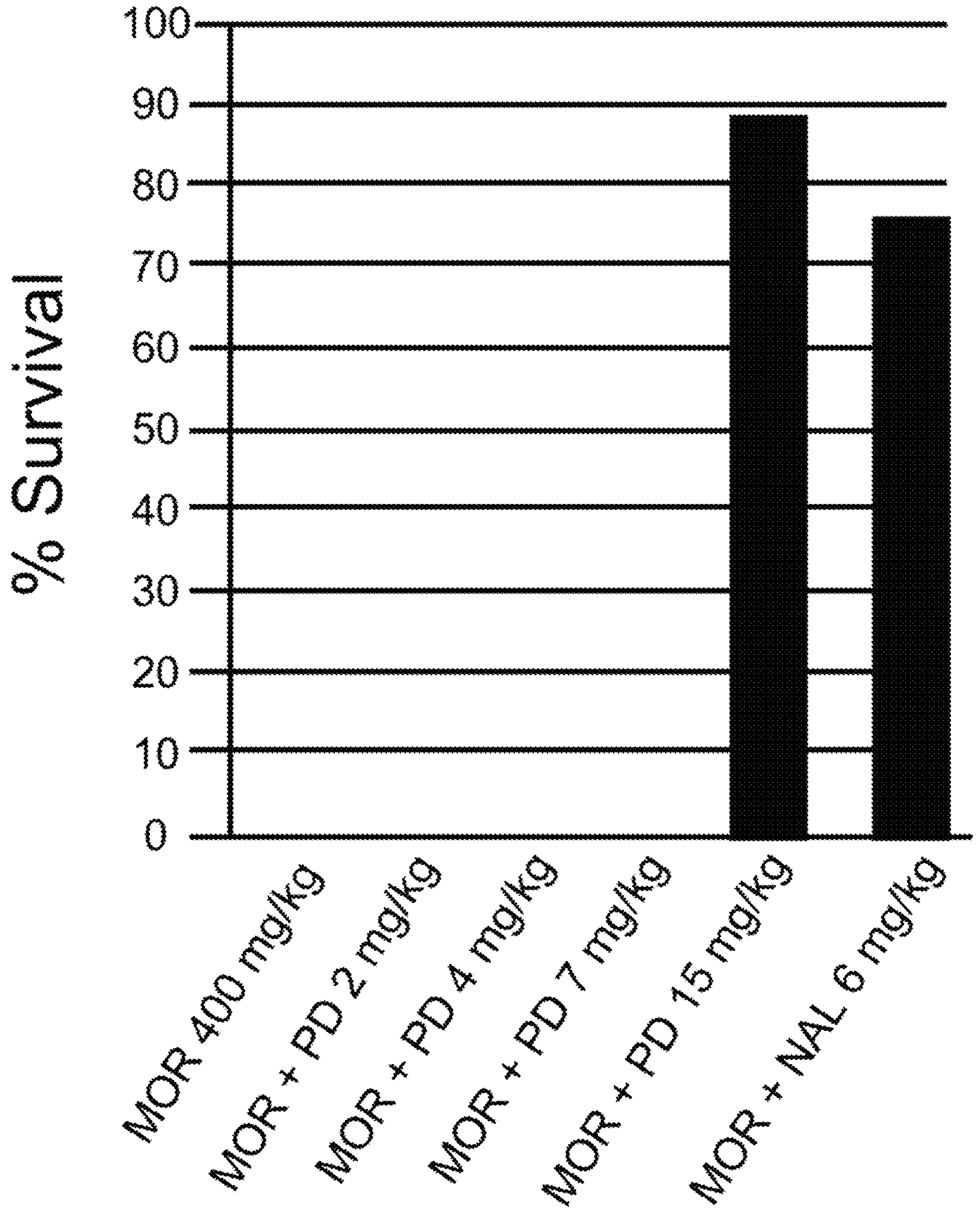
FIG. 10 is graph showing the effect of NPD-2 for a rescue of a mouse from opioid-induced respiratory failure and death.

Experiments were conducted to determine if NPD-2 can rescue a mouse from opioid-induced respiratory failure and death. Mice were administered a lethal dose of morphine by injection intraperitoneally (IP, 400 mg/kg). Fifteen minutes later mice were given variable doses of the Prodrug (as indicated) or Naloxone (6 mg/kg) also injected IP. Table 1 and FIG. 10 show the results. A survival percentage was calculated and graphed.

TABLE 1

| | # tested | # dead | Survival rate | Survival percent |
|---|---|---|---|---|
| MOR (400 mg/kg) | 2 | 2 | 0 | 0 |
| MOR + PD 2 mg/kg | 8 | 8 | 0 | 0 |
| MOR + PD 4 mg/kg | 1 | 1 | 0 | 0 |
| MOR + PD 7 mg/kg | 4 | 4 | 0 | 0 |
| MOR + PD 15 mg/kg | 8 | 1 | 0.875 | 87.5 |
| MOR + NALOXONE 6 mg/kg | 4 | 1 | 0.75 | 75 |

Example 5

Figure 11:
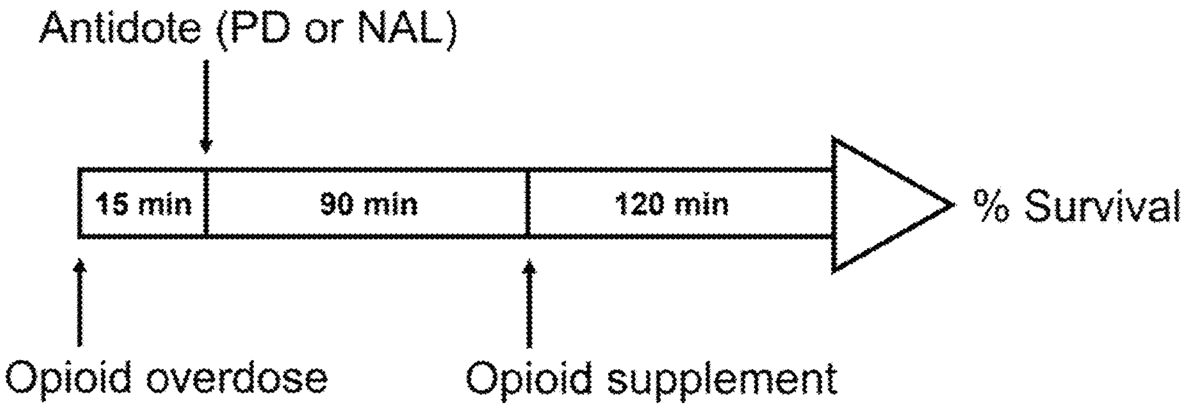
FIG. 11 is a schematic of the experimental design of Example 5.
Figure 12:
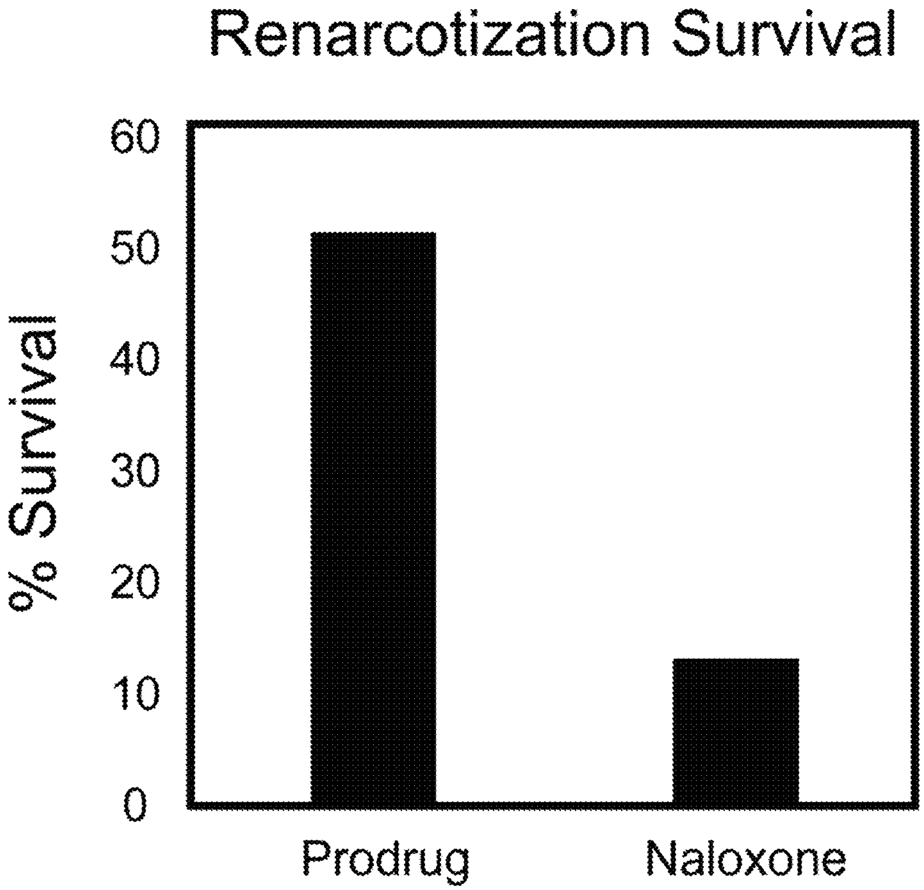
FIG. 12 is a graph showing the results of Example 5, where the prodrug of the present invention led to a higher number of surviving animals than naloxone after a supplemental opioid is given to mimic renarcotization.

Experiments were conducted to examine the effect of the prodrug of the present invention in a simulated renarcotization situation. A schematic of the experimental design is shown in FIG. 11. Doses of prodrug (15 mg/kg) and naloxone (6 mg/kg) were established to provide equivalent rescue rates after the initial opioid overdose of 80% survival. Animals surviving the initial overdose (400 mg/kg) with prodrug or naloxone were given a supplemental opioid dose (25 mg/kg). The results are shown in FIG. 12 (N=8 each group). The prodrug of the present invention led to a higher number of surviving animals than naloxone after a supplemental opioid is given to mimic renarcotization.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A modified opioid receptor antagonist compound having the following structure:

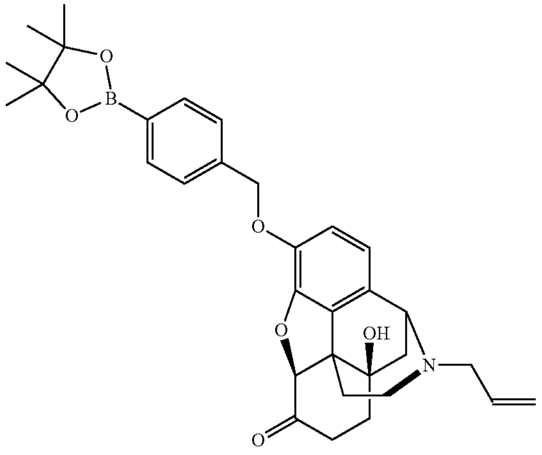

or a pharmaceutically acceptable salt thereof.

2. A modified opioid receptor antagonist compound having the following structure:

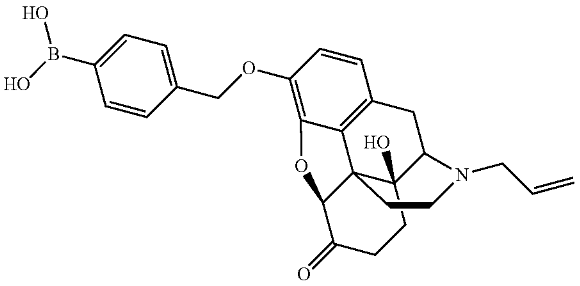

or a pharmaceutically acceptable salt thereof.

3. A method of treating opioid overdose comprising administering a therapeutically effective amount of the compound of claim 1 to a patient in need thereof, wherein administration occurs either intranasally, sublingually or intranasally and sublingually, wherein if administration occurs intranasally and sublingually administration occurs simultaneously, sequentially or concomitantly.

4. A method of treating opioid overdose comprising administering a therapeutically effective amount of the compound of claim 2 to a patient in need thereof, wherein administration occurs either intranasally, sublingually or intranasally and sublingually, wherein if administration occurs intranasally and sublingually administration occurs simultaneously, sequentially or concomitantly.

* * * * *